(12) United States Patent
Valder et al.

(10) Patent No.: US 7,214,389 B2
(45) Date of Patent: May 8, 2007

(54) PROCESS

(75) Inventors: Christopher Edmund Valder, Harlow (GB); John Peter Warr, Harlow (GB)

(73) Assignee: SmithKline Beecham, plc, Brentford, Middlesex (GB)

( * ) Notice: Subject to any disclaimer, the term of this patent is extended or adjusted under 35 U.S.C. 154(b) by 313 days.

(21) Appl. No.: 10/432,469

(22) PCT Filed: Nov. 22, 2001

(86) PCT No.: PCT/GB01/05153

§ 371 (c)(1),
(2), (4) Date: Nov. 6, 2003

(87) PCT Pub. No.: WO02/41874

PCT Pub. Date: May 30, 2002

(65) Prior Publication Data

US 2004/0070102 A1    Apr. 15, 2004

(30) Foreign Application Priority Data

Nov. 24, 2000   (GB) ................................. 0028709.4

(51) Int. Cl.
*A61K 9/14*  (2006.01)
(52) U.S. Cl. ..................................... 424/489

(58) Field of Classification Search ................. 424/489
See application file for complete search history.

(56) References Cited

U.S. PATENT DOCUMENTS

| | | | | |
|---|---|---|---|---|
| 3,885,026 A | | 5/1975 | Heinemann et al. | 424/14 |
| 4,134,943 A | | 1/1979 | Knitsch et al. | 264/28 |
| 4,792,598 A | | 12/1988 | Ziegase | 528/206 |
| 5,082,666 A | | 1/1992 | Rene et al. | 424/467 |
| 5,091,565 A | | 2/1992 | Ziegast | 562/473 |
| 5,403,593 A | * | 4/1995 | Royce | 424/489 |

FOREIGN PATENT DOCUMENTS

| | | |
|---|---|---|
| FR | 2 604 901 | 4/1988 |
| JP | 07 265682 | 10/1995 |

* cited by examiner

*Primary Examiner*—Michael Woodward
*Assistant Examiner*—Desta Yebassa
(74) *Attorney, Agent, or Firm*—Dara L. Dinner; Theodore R. Furman; Charles M. Kinzig

(57) ABSTRACT

A wet granulation process in which a pharmaceutical substance is granulated using a granulating fluid which is a halogenated hydrocarbon which has a normal boiling point below ambient temperature, for example 1,1,1,2-tetraflouroethane, under a pressure sufficient to maintain the halogenated hydrocarbon in a liquid state. A process in which the halogenated hydrocarbon is re-cycled, and suitable equipment for performing the process is also described.

21 Claims, 2 Drawing Sheets

PROCESS

Figure 1:
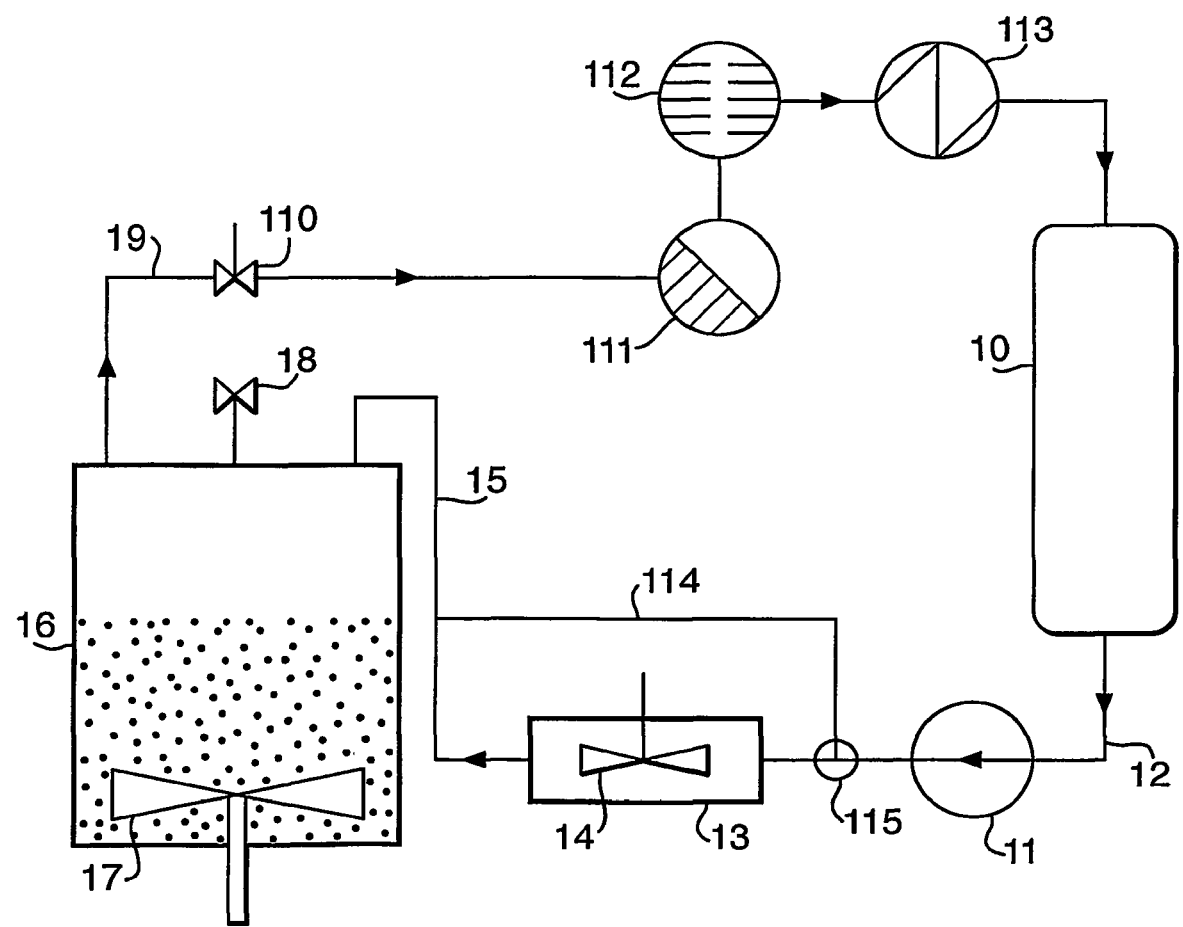

This invention relates to a novel process, being a novel process for pharmaceutical granulation.

Granulation is a process well known in the pharmaceutical industry, involving the preparation of aggregates ("granules") of fine particles of materials. Such granules are often subsequently compacted to form solid dosage forms, e.g. tablets and pills, although some pharmaceutical formulations are dispensed as granules, e.g. in a sachet for make up with water or for direct oral administration. Formulations of pharmaceutical powders are granulated for a variety of reasons falling into two main classes; processing and formulation. Processing reasons are exemplified by the need for densification and aggregation. A dense, granular material will flow more evenly and fill dies on high speed tablet machines better and with greater consistency than a simple mixture. An aggregated material will not tend to demix on storage or transport, and fine components will not be lost to extraction systems when transported through packing or processing plant. Granulation is discussed in many standard textbooks on pharmaceutical chemistry, for example "The Theory and Practice of Industrial Pharmacy", Lachman, Lieberman & Kanig, (1986).

One method of making granules is so called "wet granulation". In its simplest form, wet granulation involves the addition of a granulating fluid, commonly water, functioning as a granulating fluid, to a stirred essentially insoluble powder comprising the materials to be granulated. The stirring is essential to distribute water homogeneously through the powder bed. As the proportion of water rises, particles will absorb or adsorb water to the point where the individual particles are first saturated and then coated. After this point, liquid bridges will form between particles. At a critical point, the water content will be such that surface tension alone will pull groups of particles into aggregates. At this point water addition is halted and the powder can be dried. If the drying and subsequent handling is done with care, the aggregates will retain their integrity, giving a material which is both denser and more free flowing than the original material.

The granules can be made much more robust by the introduction of dissolved material into the liquid bridges, either by dissolving material into the granulating liquid prior to use, or by ensuring that the granulate (or a constituent thereof) is soluble or partially soluble. There are many variations on this theme, and soluble constituents (binders) can be simple polymers (PVP, starch gels) or may have more complex functions (enteric coating polymers).

Water has the advantage that it readily facilitates bridging between particles which assists agglomeration of the particles to form granules, but a major problem with wet granulation using water as the granulating fluid is that of drying. Removal of water from the wet granules can require large amounts of energy and can take a long time. Wet granulation has also been carried out with organic solvents or water-organic solvent mixtures, but even organic solvents require energy to remove them from granules, and they present fire or toxicity hazards.

It is an object of this invention to provide an improved wet granulation process which, in part at least, solves the problems of such known wet granulation processes.

It is known to use organic solvents for various processes in the manufacture of pharmaceutical formulations. For example GB-A-2197197 discloses the compaction of tablets in the presence of organic halogenated hydrocarbons, the examples illustrating processes at ambient or elevated temperatures. JP-07-265682 discloses the preparation of spherical particles by suspending powdered organic compounds in a halogenated solvent and granulating the material, the examples illustrating use of carbon tetrachloride or dichlorobenzene and water as a binder.

According to this invention a wet granulation process is provided wherein a pharmaceutical substance is granulated using a granulating fluid which is a halogenated hydrocarbon which has a normal boiling point below ambient temperature, under a pressure sufficient to maintain the halogenated hydrocarbon in a liquid state.

This invention therefore provides the use of a halogenated hydrocarbon which has a normal boiling point below ambient temperature as a granulating fluid in a wet granulation process for a pharmaceutical substance.

In the present invention the halogenated hydrocarbon is a gas at ambient temperature and atmospheric pressure, and is kept liquid during the granulation process by application of elevated pressure. The pressure at which the halogenated hydrocarbon becomes liquid by compression at ambient temperature is termed "Pv", that is, the vapour pressure.

In more detail the present invention provides a process for the granulation of a pharmaceutical substance in which;

a pharmaceutical substance in particulate form is mixed with a liquid halogenated hydrocarbon which has a normal boiling point below ambient temperature, the mixture is agitated to form granules comprising aggregates of the particles of the pharmaceutical substance, and the halogenated hydrocarbon is separated from the so-formed granules.

In the process of this invention the halogenated hydrocarbon which is a gas at room temperature and atmospheric pressure is kept liquid by pressure so that the process may be operated without the need for refrigeration. For example a suitable boiling point for the liquid halogenated hydrocarbon is −10 to −150° C., preferably −10 to −50° C., at atmospheric pressure. Preferably the halogenated hydrocarbon is a substance that can be kept liquid at temperatures up to 40° C. by applying pressures of up to 10 atmospheres. Such working conditions are relatively easy to achieve using conventional chemical engineering technology. The process of the invention may be operated at such a pressure, e.g. in a suitable pressure vessel.

Such halogenated hydrocarbons have the advantages as media for the process of the invention that they are odourless and colourless gases at ambient temperature, liquefy at around 5 bar at ambient temperature, are chemically inert, are non-flammable, are non-toxic, are non-corrosive, have a neutral pH and are approved for use in food processing by many regulatory authorities. A mixture of halogenated hydrocarbons may be used to achieve a convenient boiling point. The halogenated hydrocarbon or mixtures thereof may be mixed with other low normal boiling point compounds, e.g. low boiling point hydrocarbons such as $C_{1-5}$ alkanes, e.g. propanes and/or butanes. Suitably such mixtures may form azeotropes so that the mixture itself may be separated from the granules by evaporation at a constant temperature without fractionation. These halogenated hydrocarbons also have the advantage that they are easy to handle and re-cycle compared with higher boiling point granulating liquids, as they can be removed from a vessel containing them simply by reducing the pressure, allowing the halogenated hydrocarbon to evaporate, and then re-liquefying it with a compressor.

Suitably the halogenated hydrocarbon is a compound of formula $C_nH_mF_pCl_r$, where n and m are whole numbers, p and r are zero or whole numbers provided that both p and r are not zero and that (m+p+r) equals 2n+2. The halogenated hydrocarbon is preferably a fluorinated non-chlorinated hydrocarbon. Preferably the halogenated hydrocarbon is a compound of formula $C_nH_mF_p$ where n, m and p are whole numbers and (m+p) equals 2n+2.

The lower and upper limits of n are determined more by the practical considerations of achieving the above-mentioned liquefaction characteristics, and typically n is between 1 and 10. Preferably in such a compound n is 2 or 3, preferably 2 so that the compound is an ethane derivative, preferably p is 3, 4 or 5, especially 4 so that the compound is a tetrafluoroethane. A particularly preferred fluorinated hydrocarbon is 1,1,1,2-tetrafluoroethane (bp. −26° C., critical temperature +101° C.). This material is commercially available (from ICI) under the name R134A, and is otherwise known for use as a refrigerant. R134A is 1,1,1,2-tetrafluoroethane sold to a high purity specification and contains no significant amounts of other fluorocarbons or organic solvents. The highest specification 1,1,1,2-tetrafluoroethane that is sold is P134A, "P" standing for pharmaceutical grade, e.g. as used as a propellant in inhalers. It is not believed to be necessary to use the P134A grade of 1,1,1, 2-tetrafluoroethane in the process of this invention.

Other suitable halogenated hydrocarbons include fluoroform, monofluoromethane, difluoromethane, trifluoromethane, pentafluoroethane, 1,1,1-trifluoroethane, 1,1-difluoroethane, 1,1,1,2,3,3,3-heptafluoropropane, 1,1,1,2,2,3, 3-heptafluoropropane, 1,1,1,3,3,3-hexafluoropropane, 1,1,1, 2,2-pentafluoropropane, 1,1,1,2,2,3-hexafluoropropane, 1,1, 2,2,3,3-hexafluoropropane, and 1,1,1,2,3,3-hexafluoropropane. A suitable fluorinated and chlorinated hydrocarbon is difluorodichloromethane. Some other examples of halogenated hydrocarbons include 2,2-difluoropropane (bp. −0.6° C.) and 1,1-difluoroethane (bp. −24.7° C.)

The process of the present invention appears to be suitable for all types of drug substance, e.g. antibiotics, antidepressants, anti-inflammatories, antiviral agents, analgesics, substances for the treatment of diabetes etc.

In pharmaceutical granules the drug substance is normally mixed with standard excipients such as one or more of a filler, a lubricant, a disintegrant, a glidant, a colourant, a flavour or flavour modifier etc. Examples of these are well known and are listed in standard texts such as for example Lachman, Lieberman & Kanig (op cit.) and the process of the invention appears to be suitable for the granulation of pharmaceutical substances which comprise a drug substance mixed with one or more of such excipients.

It may be possible to use the process of this invention for granulating the substance without a binder, but preferably in the process the pharmaceutical substance includes a binder. Suitable binders are known and listed in for example the above-mentioned standard texts. A preferred binder is one that is soluble in the halogenated hydrocarbon. As the process of the invention can be operated in a manner that recycles the halogenated hydrocarbon over the binder to re-saturate the recycled halogenated hydrocarbon with the binder so as to transfer it to the pharmaceutical substance, the process can operate even when the binder is only slightly soluble in the halogenated hydrocarbon, for example at solubilities of 1 % w:w, 0.25% w:w or even lower of the binder in the halogenated hydrocarbon.

Preferred binders therefore include low molecular weight (e.g. <10,000) polymeric binders, for example polyethers; cellulose-based polymers such as methylcelluloses, ethylcelluloses; polyvinylpyrrolidones (e.g. Kollidons), acrylate and methacrylate polymers for example the polymer materials available from Röhm GmbH under the trade mark "Eudragit", e.g. Eudragit RS, Eudragit E, etc., polyacrylamides, vinylic polymers such as polyvinyl achohols, esters etc.

The proportion of binder in the granulated product made by the process of this invention may be the same as would be used in a conventional granulation process and a suitable proportion may be determined by experiment. For example in some applications, such as when granulation is used to taste mask a highly soluble drug substance, the granulated product may comprise 50% w:w or more of the granulated product, though other applications may use less binder. The process of the invention itself does not appear to impose or require any limits on the proportion of binder in the granulated product.

A binder when used may be made into a mixture with the pharmaceutical substance in a number of ways. For example the binder may be pre-mixed with the particles of pharmaceutical substance, and then the halogenated hydrocarbon may be mixed with this pre-mix. Some common binders are available in solution form, and they may be pre-mixed with the substance in this form. Typically this might be a batch process. For example the binder may be dissolved or suspended in the halogenated hydrocarbon, and this solution or suspension may be mixed with the pharmaceutical substance.

In a preferred way, the halogenated hydrocarbon is passed over the binder in a saturator vessel to form a solution, preferably a saturated solution, of the binder and this solution is then introduced to the pharmaceutical substance in a suitable granulator vessel. The halogenated hydrocarbon may then be removed by evaporation from the mixture of substance and binder and then re-liquefied e.g. by elevating the pressure and/or lowering the temperature, in a condenser, and passed over the binder again to dissolve further binder, preferably to be re-saturated with binder, then this recycled solution is added to the substance in the granulator vessel, i.e. in a cyclic process, until all or sufficient binder has been mixed into the pharmaceutical substance.

Such a recycling process, in which the halogenated hydrocarbon is re-circulated via a condenser and pump, passed through a saturator loaded with binder, and then passed back into the granulator may be advantageous when the solubility of the binder in the halogenated hydrocarbon is low, in which case such a recycling process can steadily transfer a relatively insoluble binder into the granulator vessel.

It may be possible to increase the solubility of binders by incorporating entraining or modifying solvents into the halogenated hydrocarbon, and such a mixture of halogenated hydrocarbon and solvent can be handled in the same way as a pure halogenated hydrocarbon in the process of this invention. However purging of the product granules using pure halogenated hydrocarbon may be required to remove traces of such solvents. If such a mixture is used preferably the mixture is an azeotropic solvent mixture, so that the solvent may be removed at ambient pressure and temperature together with the halogenated hydrocarbon. Examples of suitable entraining or modifying solvents include water, C1–10 aliphatic alcohols, ketones or esters, typically if used comprising 0.5–10 % v:v of the halogenated hydrocarbon, solvent mixture. For example polymethacrylate binders such as the Eudragit™ materials are soluble in propanol, acetone and propanol—acetone mixtures.

The particle sizes, grades, .size distribution etc. for the pharmaceutical substance, e.g. a drug substance, excipients and binder, if used, may be similar or identical to those used in conventional wet granulation processes. Typically such materials are provided for granulation as powders with a particle size of ca. 500 microns or less, and the process of granulation generates agglomerated granules with a granule size larger than this.

The ratio of halogenated hydrocarbon to pharmaceutical substance to be granulated does not appear to be critical and the process appears to be operable over a wide range of ratios ranging from a fluid suspension through a viscous moistened, e.g. dough-like mass to a light "crumb" (term of the art). However a highly viscous mass may have the disadvantage of needing a high power requirement to agitate and thoroughly mix the ingredients, and an excess of the halogenated hydrocarbon will take longer to separate from the mixture than a smaller amount. Typically the mixture of pharmaceutical substance and halogenated hydrocarbon may contain 0.01 to 99.9% w:w, for example <5 to 95% w:w of the halogenated hydrocarbon. Suitable ratios, and other operating conditions such as processing time, operating power, granulator equipment construction etc., for any particular pharmaceutical substance may be determined experimentally by techniques well known to those skilled in the art of pharmaceutical granulation. For example progress toward completion of the granulation process may be determined simply by removal and inspection of a sample of the mixture from the mixing vessel in which the process is being performed. Alternatively progress may be followed by monitoring power consumption of the agitator, e.g. the stirrer motor of the granulation vessel. Alternatively, infra red, acoustic and image analysis or other non-intrusive techniques may also be employed.

As the halogenated hydrocarbon has a normal boiling point below room temperature it is preferably separated from the granules by reduction of the pressure so that the halogenated hydrocarbon evaporates off from the granules. This evaporation is preferably performed in a closed system so the evaporated halogenated hydrocarbon may be led away along a flow line to a suitable receiver e.g. via a condenser as above-mentioned. The reduction of pressure may be controlled so that smooth evaporation of the halogenated hydrocarbon occurs. Thereafter purging e.g. with nitrogen can ensure removal of further traces of the halogenated hydrocarbon if necessary.

After separation of the halogenated hydrocarbon from the granules, these may be further processed in other ways. For example they may be subdivided, screened etc. before ultimate use e.g. compaction into tablets etc. Such further processing may be identical or similar to further processing as used with conventional wet granulation processes.

On an industrial scale, conventional granulating equipment may conveniently be adapted to run the process of the invention. For example a generally conventional granulator may be provided with a closure, means to maintain a suitable pressure within it, means to introduce the halogenated hydrocarbon, and means to remove the halogenated hydrocarbon.

Such a granulator may comprise a pressurised vessel based upon a conventional sigma blade, heavy duty planetary mixer, or high intensity mixer (Fielder, Collette), and which may be capable of granulating 100 to 200 kg. of material, depending on the density of the powders and the consistency of the resulting wetted mass. For bench scale work a suitable granulator may be based on a small scale Caleva spheronizer. The spheronizer disk may be removed and replaced with a double scimitar chopping blade or impeller after the conventional model. Other methods of agitation, such as ultrasonic agitation may be used. A closure may be fitted on the pressure vessel, equipped with inlet and outlet ports (e.g. ⅛ Swage-Lok). The lid may also be also fitted with a window and pressure relief valve (typically 10 bar spec). The equipment may also be fitted with a power consumption monitor, and may be jacketed for temperature control.

In use, binder e.g. a polymer as mentioned above may be dissolved in the halogenated hydrocarbon in an agitated, e.g. stirred, dissolution vessel equipped with a pressure gauge. halogenated hydrocarbon may be pumped into this vessel from a separate source vessel until a suitable liquid level is reached, and the halogenated hydrocarbon is saturated with the binder, then the saturated solution may be pumped into the granulator vessel. The dissolution vessel may be jacketed in common with the mixer vessel to ensure that temperature (and Pv) are the same.

A preferred configuration of equipment to perform the process of this invention comprises;

a source of halogenated hydrocarbon (optionally mixed with one or more of the above-mentioned solvents), means such as a pump to transfer halogenated hydrocarbon from the source to a saturator vessel, a saturator vessel, in use being loaded with a binder, and able to bring halogenated hydrocarbon and binder into contact to generate a solution of the binder in the halogenated hydrocarbon, means such as a pump to transfer the solution of binder in the halogenated hydrocarbon to a granulator vessel and to pressurise the granulator vessel, a granulator vessel in which the pharmaceutical substance in particulate form to be granulated is mixed with the liquid halogenated hydrocarbon to form granules comprising aggregates of the particles of the pharmaceutical substance, the vessel being equipped with means of controlling the pressure of the granulating fluid inside it.

means to remove the halogenated hydrocarbon from the granulator vessel in a gaseous state, a compressor to compress the gaseous halogenated hydrocarbon, a condenser by which the halogenated hydrocarbon is converted to a liquid state, means to return the liquid halogenated hydrocarbon to the source.

Optionally this equipment may include a trap situated upstream of the compressor to remove entrained material from the flow of gaseous halogenated hydrocarbon.

The present invention therefore provides a granulation process wherein a pharmaceutical substance is granulated using such equipment.

The present invention also provides a granulated pharmaceutical substance obtainable by a process as described herein. Such a granulated substance may contain a trace of residual fluorinated hydrocarbon.

The invention will now be described by way of example only with reference to:

FIG. 1 which shows schematically a configuration of equipment for performing the process of this invention.

Figure 2:
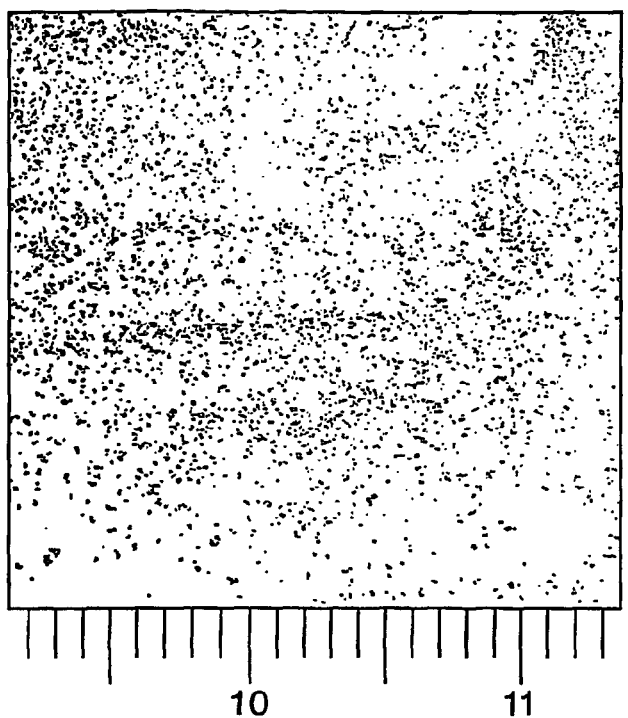

FIG. 2 which shows particulate material before granulation using the process of this invention.

Figure 3:

FIG. 3 which shows the material of FIG. 2 after granulation using the process of this invention.

Referring to FIG. 1, a schematic configuration of equipment is shown. This comprises a source (10) of halogenated hydrocarbon being a pressurised tank. The halogenated hydrocarbon used is R134A, a commercially available mixture of 1,1,1,2-tetrafluoroethane and other organic solvents, available from ICI. R134A is a gas at room temperature, but can be easily liquefied at a pressure of 10 bar at temperatures as high as 40° C. From the tank (10) the R134A is pumped by pump (11) via line (12) to a saturator vessel (13).

Saturator vessel (13) is a conventional extraction vessel, and is loaded with a known polymeric binder such as a Eudragit™, for example Eudragit RS™ or Eudragit E™, or a known polyvinylpyrrolidone polymer, e.g. as commercially available under the name "Kollidon™". In the saturator (13) the halogenated hydrocarbon pumped into the saturator (13) and the binder are brought into contact, and may be agitated by stirrer (14), so that the binder dissolves in the halogenated hydrocarbon. The solution of binder in the halogenated hydrocarbon may be saturated or undersaturated.

From the saturator (13) the continued action of the pump (11) transfers the saturated solution of the binder in the halogenated hydrocarbon via line (15) into the granulator vessel (16).

The granulator vessel (16) is a granulator vessel of generally conventional construction, e.g. of the conventional sigma blade, heavy duty planetary mixer, or high intensity mixer (Fielder, Collette) type, and may typically be capable of granulating 100 to 200 kg. of material. The vessel (16) is provided with a closure etc. to enable a pressure of ca. 10 bar, i.e. sufficient to keep the R134A in a liquefied state at ambient temperature to be maintained. A pharmaceutical substance in particulate form to be granulated has previously been loaded into the vessel (16). This substance may be a typical mixture of a drug substance and excipients (with the exception of a binder insofar as this is provided as the above-mentioned solution). The mixture of pharmaceutical substance and the saturated solution is agitated in the vessel by the mixing blade (17). The vessel (16) is provided with a pressure relief valve (18) for safety.

Gaseous R134A evaporates off from the mixture in the vessel (16) and is bled off via line (19), pressure being regulated by means of the pressure regulator (110). The vapour is passed through trap (111) to remove e.g. solid particles etc entrained in the vapour, and is then compressed by compressor (112), and condensed by condenser (113) back into liquid form. The liquid R134A is then transferred back into the vessel (10), from whence it can be recycled into granulator vessel again via line (12), pump (11) and saturator (13).

As this recycled R134A is passed through the saturator (13) it will become re-saturated with the binder and thereby transfers more binder into vessel (16), so that the amount of binder in granulator (16) gradually builds up to an appropriate level to form the granules. A steady state is achieved in which an approximately constant level of liquid R134A is maintained in granulator (16) by controlled bleeding out via line (19) and controlled re-cycling of the R134A.

The progress of granulation of the substance in the granulator vessel (16) may be monitored by conventional methods, e.g. withdrawal of a sample from granulator vessel (16) or by monitoring of power consumption of the mixer blade (17). When granulation is considered complete the re-cycling of R134A is stopped, and remaining R134A is separated from the granules in granulator vessel (16) by reduction of pressure in the granulator vessel (16) and bleeding the remaining R134A out of granulator (16) via line (19).

If for example a mixture of a halogenated hydrocarbon and an organic solvent is used as the granulating fluid, it might be necessary to purge residual traces of the organic solvent from the granulator vessel (16) by passing pure halogenated hydrocarbon through the vessel (16). The system may also include a by-pass line (not shown) by which halogenated hydrocarbon granulating fluid may be introduced directly into the granulator vessel (16) without passing through the saturator (13) to enable the granulator vessel (16) to be pressurised with the halogenated before introducing the binder to vessel (16).

After this the pressure in granulator (16) may be reduced to atmospheric, the halogenated hydrocarbon or R134A itself purged with air, and the so-formed granules may be removed from the granulator (16) and further processed e.g. by a conventional compaction process to form tablets.

LABORATORY EXAMPLE

An inert filler material, manitol (Perlitol 200 SD, Roquette) was loaded into a vessel (For example, a 100 cm$^3$ Pamasol™ Aerosol Test Glasses, type P200/002) fitted with a gas tight valve together with an appropriate amount of polymer binder, to a total weight of 2.0 g of the mixed filler and binder. The vessel was charged with 40 cm3 of R134A, and thoroughly mixed. The vessel was then placed in an ultrasonic bath at 40° C. for 15 minutes to ensure dissolution of the polymer, then shaken well. The vessel was returned to the ultrasonic bath for a further 15 minutes. The ultrasound was then turned off, the pressure valve was opened and the R134 was allowed to evaporate. The aggregated material was then recovered. No physical work was put into the granule and no post granulation size reduction carried out.

The following polymeric binder materials were used:
Kollidon 12™
Kollidon 17™
Eudragit RS PO™
Eudragit E 100™
Erkopol B-1.5™
Erkopol B-17™

These were all used at 10, 20 and 30% w/w of the overall mannitol—binder mixture.

The degree of granulation was assessed by shaking the materials over a pair of nested sieves, 1000 and 500 microns. 100% of Perlitol 200 sd passes through a 500 micron sieve. The % retained >500 microns gives a measure of agglomeration.

|  | % retained 1000 mic. | % retained 500 mic. | % retained Base | % retained >500 mic. |
| --- | --- | --- | --- | --- |
| Kollidon 12 @ 10% | 21.5 | 2.7 | 75.9 | 24.1 |
| Kollidon 12 @ 20% | 17.0 | 17.4 | 65.6 | 34.4 |
| Kollidon 12 @ 30% | 55.7 | 10.2 | 34.0 | 66.0 |
| Kollidon 17 @ 10% | 1.0 | 2.8 | 96.2 | 3.8 |
| Kollidon 17 @ 20% | 8.1 | 1.4 | 90.5 | 9.5 |
| Kollidon 17 @ 30% | 17.0 | 24.4 | 58.6 | 41.4 |
| Eudragit RS100PO 10% | 57.2 | 5.5 | 37.3 | 62.7 |
| Eudragit RS100PO 20% | 51.8 | 10.1 | 38.1 | 61.9 |
| Eudragit RS100PO 30% | 69.5 | 10.6 | 19.9 | 80.1 |
| Eudragit E100 10% | 35.5 | 19.2 | 45.2 | 54.8 |
| Eudragit E100 20% | 56.2 | 18.0 | 25.8 | 74.2 |
| Eudragit E100 30% | 46.6 | 20.7 | 32.7 | 67.3 |

Referring to FIGS. 2 and 3, these respectively show Perlitol 200 SD, (Roquette) in particulate form both prior to granulation in the laboratory example described above (FIG. 2) and after granulation using 30% Eudragit RS100PO as binder. It is seen that the particulate material has been converted into large granules in the process of the invention.

Erkopol materials were granulated so effectively that in some experiments the product had to be dug out of the vessel at these levels of polymer addition.

The invention claimed is:

1. A wet granulation process wherein a pharmaceutical substance is formed into a granulate using a granulating fluid which is a halogenated hydrocarbon having a normal boiling point below ambient temperature, under a pressure sufficient to maintain the halogenated hydrocarbon in a liquid state.

2. A process according to claim 1 wherein;
   the pharmaceutical substance in particulate form is mixed with the liquid halogenated hydrocarbon having a normal boiling point below ambient temperature, and
   the mixture is agitated to form granules comprising aggregates of the particles of the pharmaceutical substance, and
   the halogenated hydrocarbon is separated from the so-formed granules.

3. A process according to claim 1 wherein the halogenated hydrocarbon has a normal boiling point +20° C. to −150° C. at atmospheric pressure.

4. A process according to claim 1 wherein the halogenated hydrocarbon is a compound of formula $C_nH_mF_pCl_r$, where n and m are whole numbers, p and r are zero or whole numbers provided both p and r are not zero and (m+p+r) equals 2n+2.

5. A process according to claim 4 wherein the halogenated hydrocarbon is a compound of formula $C_nH_mF_p$ where n, m and p are whole numbers and (m+p) equals 2n+2.

6. A process according to claim 5 wherein n is 2 or 3, and p is 3, 4 or 5.

7. A process according to claim 6 wherein the halogenated hydrocarbon is 1,1,1,2 - tetrafluoroethane.

8. A process according to claim 1 wherein the pharmaceutical substance further includes a binder.

9. A process according to claim 8 wherein the binder is soluble in the halogenated hydrocarbon.

10. A process according to claim 8 wherein the binder is a low molecular weight polymeric binder.

11. A process according to claim 8 wherein the binder is selected from polyethers, cellulose-based polymers, polyvinylpyrrolidones, acrylate and methacrylate polymers.

12. A process according to claim 9 wherein the binder is pre-mixed with the particles of pharmaceutical substance, and then the halogenated hydrocarbon is mixed with this pre-mix.

13. A process according to claim 8 wherein the binder is dissolved or suspended in the halogenated hydrocarbon, and this solution or suspension is mixed with the pharmaceutical substance.

14. A process according to claim 13 wherein a) the halogenated hydrocarbon is passed over the binder in a saturator vessel to form a solution of the binder, and
   b) the solution is then introduced to the pharmaceutical substance in a vessel, and
   c) the halogenated hydrocarbon is then evaporated from the mixture of substance and binder, then re-liquefied and passed over the binder again to dissolve further binder, and
   d) the recycled solution of binder in the halogenated hydrocarbon, from part c is added to the substance in the granulator vessel, in a cyclic process.

15. A process according to claim 1 wherein entraining or modifying solvents are further incorporated into the halogenated hydrocarbon.

16. A process according to claim 1 wherein the halogenated hydrocarbon is separated from the granules by reduction of the pressure so that the halogenated hydrocarbon evaporates off from the granules.

17. Equipment to perform the process according to claim 1 comprising;
   a source of halogenated hydrocarbon,
   means to transfer halogenated hydrocarbon from the source to a saturator vessel,
   an extraction vessel, in use being loaded with a binder, and able to bring halogenated hydrocarbon and binder into contact to generate a solution of the binder in the halogenated hydrocarbon,
   means to transfer the solution of binder in the halogenated hydrocarbon to a granulator vessel,
   a granulator vessel in which the pharmaceutical substance in particulate form to be granulated is mixed with the liquid halogenated hydrocarbon to form granules comprising aggregates of the particles of the pharmaceutical substance,
   means to remove the halogenated hydrocarbon from the granulator vessel in a gaseous state,
   a compressor to compress the gaseous halogenated hydrocarbon,
   a condenser by which the halogenated hydrocarbon is converted to a liquid state, and means to return the liquid halogenated hydrocarbon to the source.

18. A granulated pharmaceutical substance obtainable by a process according to claim 1.

19. A process according to claim 15 wherein the entraining or modifying solvents are selected from water, $C_1$-10 aliphatic alcohols, ketone or esters.

20. A process according to claim 19 wherein the entraining or modifying solvent is propanol, acetone, and a propanol/acetone mixture.

21. A process according to claim 10 wherein the low molecular weight polymeric binder is selected from a polyacrylamide, or a vinylic polymer.

* * * * *